(12) United States Patent
Rodenfels (10) Patent No.: US 8,919,383 B2
(45) Date of Patent: Dec. 30, 2014

(54) DEVICE AND METHOD FOR MANIPULATING A LIQUID (75) Inventor: Tobias Rodenfels, Dortmund (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 259 days.

(21) Appl. No.: 13/583,785

(22) PCT Filed: Mar. 14, 2011

(86) PCT No.: PCT/EP2011/001242
§ 371 (c)(1),
(2), (4) Date: Oct. 24, 2012

(87) PCT Pub. No.: WO2011/113563
PCT Pub. Date: Sep. 22, 2011

(65) Prior Publication Data
US 2013/0206264 A1 Aug. 15, 2013

(30) Foreign Application Priority Data
Mar. 15, 2010 (EP) .................................. 10002685

(51) Int. Cl.
F15C 3/00 (2006.01)
B01L 3/00 (2006.01)
G01N 33/543 (2006.01)
F16K 99/00 (2006.01)
G01N 33/53 (2006.01)

(52) U.S. Cl.
CPC ....... *F16K 99/0017* (2013.01); *B01L 2400/043* (2013.01); *B01L 3/5027* (2013.01); *B01L 2300/0636* (2013.01); *B01L 3/502769* (2013.01); *G01N 33/54326* (2013.01); *G01N 33/54366* (2013.01); *B01L 3/50273* (2013.01); *G01N 33/5304* (2013.01); *B01L 2400/0475* (2013.01); *B01L 2400/0688* (2013.01); *B01L 2200/0647* (2013.01)
USPC .............. 137/832; 137/829; 137/833; 251/65

(58) Field of Classification Search
USPC ................. 137/832, 833, 829, 247, 248, 246, 137/246.23, 246.12; 251/65
See application file for complete search history.

(56) References Cited

U.S. PATENT DOCUMENTS 5,439,650 A 8/1995 Tsugita et al.
5,458,852 A * 10/1995 Buechler ....................... 422/417
(Continued)

FOREIGN PATENT DOCUMENTS

DE 102004062534 A1 7/2006
EP 1441131 A1 7/2004
(Continued)

OTHER PUBLICATIONS

"GERDA icing and pastry injectors". teenagewasteland.e, 1950, 2 pages. [Accessed at http://www.teenagewasteland.de/haushalt/d_tortenspritze.html on May 9, 2011].

(Continued)

*Primary Examiner* — John Rivell
*Assistant Examiner* — Minh Le
(74) *Attorney, Agent, or Firm* — Michael P. Morris; Joyce L. Morrison (57) ABSTRACT The invention relates to a device and method for manipulating a liquid in a channel, wherein a body, which forms a capillary intermediate space with respect to the channel wall, is moved in the channel and the channel is filled with liquid only up to the body. Preferably, the body can also bridge an area of the channel that cannot be wetted for the liquid.

9 Claims, 4 Drawing Sheets

(56) References Cited

U.S. PATENT DOCUMENTS

| | | | |
|---|---|---|---|
| 6,143,248 A * | 11/2000 | Kellogg et al. | 422/72 |
| 6,296,020 B1 * | 10/2001 | McNeely et al. | 137/806 |
| 6,360,775 B1 * | 3/2002 | Barth et al. | 137/828 |
| 6,521,188 B1 * | 2/2003 | Webster | 422/504 |
| 7,134,453 B2 | 11/2006 | Peters et al. | |
| 7,156,117 B2 * | 1/2007 | Bohm | 137/14 |
| 7,412,990 B2 * | 8/2008 | Chung et al. | 137/833 |
| 7,547,415 B2 * | 6/2009 | Hataoka et al. | 422/552 |
| 7,802,591 B2 * | 9/2010 | Barrow et al. | 137/806 |
| 7,833,486 B2 * | 11/2010 | Fielden et al. | 422/502 |
| 7,897,113 B2 * | 3/2011 | Weng et al. | 422/106 |
| 2005/0045238 A1 * | 3/2005 | Yang et al. | 137/833 |
| 2005/0133101 A1 * | 6/2005 | Chung et al. | 137/833 |
| 2007/0034270 A1 * | 2/2007 | Yang et al. | 137/833 |
| 2010/0000620 A1 * | 1/2010 | Fouillet et al. | 137/827 |
| 2010/0101660 A1 * | 4/2010 | Kitamura et al. | |
| 2012/0168016 A1 * | 7/2012 | Oh et al. | 137/828 |
| 2012/0180894 A1 * | 7/2012 | Sugahara | 137/827 |
| 2013/0156643 A1 | 6/2013 | Rodenfels et al. | |
| 2013/0206264 A1 | 8/2013 | Rodenfels | |

FOREIGN PATENT DOCUMENTS

| | | |
|---|---|---|
| GB | 02130 | 0/1908 |
| GB | 21439 | 0/1909 |
| WO | 2003072252 A1 | 9/2003 |
| WO | 2007089564 | 4/2007 |
| WO | 2008036997 A1 | 4/2008 |
| WO | 2009044088 A1 | 4/2009 |
| WO | 2011113563 A1 | 9/2011 |
| WO | 2011113569 A1 | 9/2011 |

OTHER PUBLICATIONS

"Integrated Microfluidic Diagnosis Systems—IMIKRID". Federal Ministry for Education and Research, May 31, 2010, pp. 1-2. [Accessed at http://www.mstonline.de/foerderung/projektliste/printable_pdf?vb_nr=W3BI0057 on Jul. 6, 2010].

"Pistons". Works Association—Association for Preservation of the Historic Aircraft Works in Schleissheim, 1936, 2 pages. [Accessed at http://www.der-werftverein.de/akr/jumo205c/jumo205_kolben.html on May 4, 2011].

"Water Level Indicator"., Hydrotip.de, Mar. 9, 2001, 1 page. [Accessed at http://www.hydrotip.de/friends3/parser.php? uid=253 on May 4, 2011].

Forrester et al., "Identification of Adenosine Triphosphate in Human Plasma and the Concentration in the Venous Effluent of Forearm Muscles Before, During and After Sustained Contractions". The Journal of Physiology, vol. 204, Oct. 1969, pp. 347-364.

International Search Report and Written Opinion for PCT/EP2011/001242 mailed Aug. 19, 2011.

Karle et al., "Continuous Microfluidic Platform for the purification of biomolecules". Microsystems Technology Congress, Oct. 2009, pp. 1-4. [Accessed at http://www.imtek.de/content/pdf/public/2009/kontinuierlich_arbeitende_mikrofluidik-plattfo.pdf on Jul. 5, 2010].

Sawetzki, T., "Microparticles as Active Components of Microfluidic Operations". From the Faculty of Mathematics and Physics, University of Stuttgart Approved idssertation submitted to attain the degree of Doctor of Natural Sciences, Dec. 14, 2009, p. 35 and p. 60. [Accessed at http://elib.uni-stuttgart.de/opus/volltexte/2010/4899/ on Jul. 5, 2010].

Tullis et al., "Non-Wettable Surfaces". Blood, vol. 7, No. 8, Aug. 1952, pp. 850-853.

Mandy et al., "Flow Cytometry". Biomedical Photonics Handbook, vol. 125, Chapter 25, Section 25.11, CRC Press, 2003, 20 pages.

* cited by examiner

DEVICE AND METHOD FOR MANIPULATING A LIQUID

The present invention relates to a device for manipulating a liquid according to the preamble of claim 1, and a method for manipulating a liquid according to the preamble of claim 10.

The present invention relates particularly to the manipulation of a liquid in a microfluidic system or channel. It is known to use a valve or selective venting, for example, for manipulating the liquid. In this way the liquid can be stopped in particular at a specific point. The control or manipulation of the front of the liquid, particularly in a desired region of the channel, on the other hand, is difficult or involves additional effort.

The problem on which the present invention is based is to provide a device and a method for manipulating a liquid in a preferably microfluidic channel, by which an improvement in the manipulation, particularly of the flowing front of the liquid, is made possible or facilitated.

This problem is solved by a device according to claim 1 or a method according to claim 10. Advantageous further features are the subject of the sub-claims.

In one aspect the present invention envisages providing or moving a body in a channel for the liquid, wherein a capillary gap or intermediate space is formed between the body and the channel wall, the liquid or its front is stopped in the gap or intermediate space by capillary forces and the channel only fills up with the liquid as far as the body or only up to the end of the gap or intermediate space, while the filling of the channel with the liquid is controlled or manipulated by the position and/or movement of the body. This makes it very easy to obtain and manipulate the flowing front—hereinafter also referred to as the "front" for short—of the liquid.

Preferably, the body fills the channel by more than 60%, in particular more than 70%, particularly preferably more than 80%, of the cross-sectional area. As a result, particularly high capillary forces can be achieved between the body and the channel wall.

In another aspect of the present invention, the body is moved over a region of the channel that cannot be wetted by the liquid and this region is bridged for the liquid so that the liquid flows or is able to flow over this region. This again allows very simple control or manipulation of the liquid or its front.

According to another aspect of the present invention, the body can be moved selectively or successively into different sections of the channel or into a channel that branches off from the channel, in order to selectively control the filling with liquid.

According to another aspect of the present invention, a side channel may branch off from the channel, and the liquid only flows or is able to flow in the side channel when the body is moved, or has been moved, with the liquid in the channel at least up to the branching-off of the side channel. In this way, too, it is possible to achieve selective control of the filling with the liquid in a simple manner.

Preferably, the body is guided in or by the channel in a defined alignment. In particular, the body cannot be rotated within the channel.

Preferably, the body has a length that is greater than the maximum cross section of the channel. This allows a defined movement and/or direction of the body in the channel or microfluidic system.

Preferably, the body is dimensionally stable with a defined shape.

The present invention relates to the manipulation of a liquid, particularly in a microfluidic channel or system. By "microfluidic" are meant, according to the invention, volumes of preferably less than 10 ml, particularly preferably less than 1 ml, and/or channel liquid cross-sections (maximum diameters) of preferably less than 2 mm, particularly preferably less than 500 µm.

The above-mentioned aspects of the present invention and the aspects and features of the present invention that arise from the following description and the claims may be implemented independently of one another, or in any desired combination.

Further aspects, features, properties and advantages of the present invention will become apparent from the claims and the following description of preferred embodiments by reference to the drawings, wherein:

In the Figures, the same reference numerals have been used for identical or similar parts and components, producing corresponding or similar advantages and properties, even if the description is not repeated.

Figure 1:
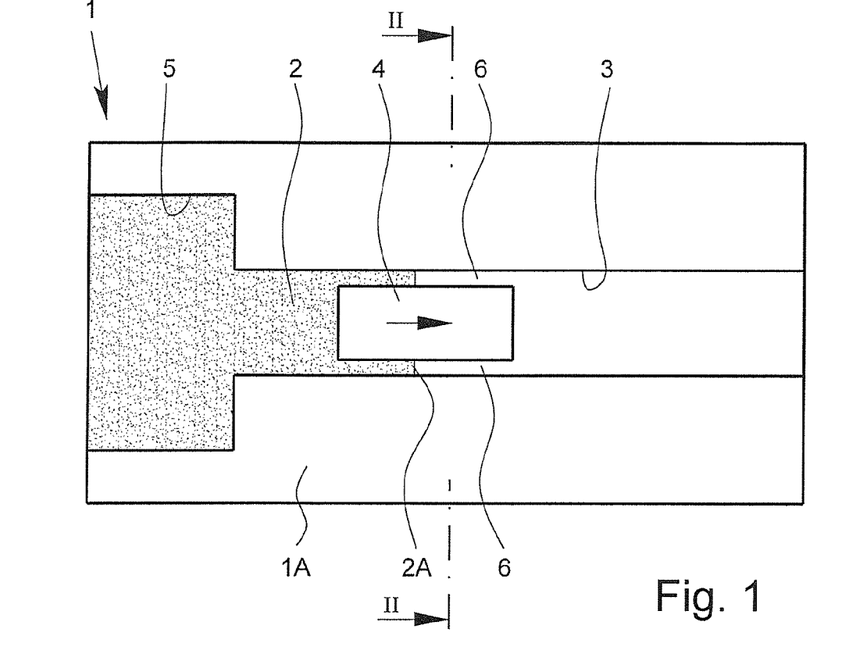
FIG. 1 shows a plan view of a proposed device according to a first embodiment.

FIG. 1 shows in schematic plan view a proposed device 1 for manipulating a liquid 2. The device 1 is preferably at least substantially card-shaped, plate-shaped, flat, thin and/or planar in configuration.

The device 1 preferably has (at least) one in particular microfluidic channel 3 for receiving the liquid 2. The channel 3 or the device 1 forms, in particular, a microfluidic system or a part thereof.

Figure 2:
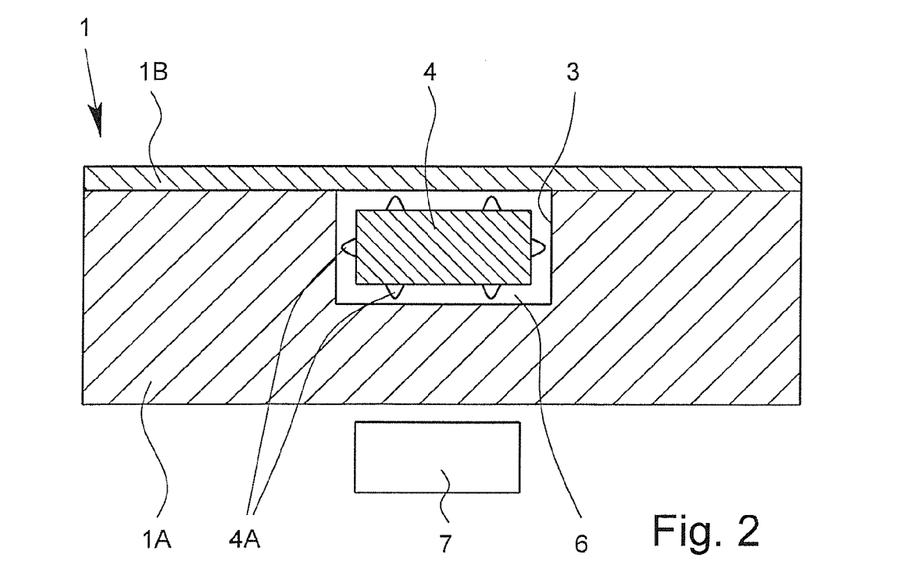
FIG. 2 is a schematic cross-section of the device according to the first embodiment.

As shown in a schematic cross section of the device 1 according to FIG. 2, the device 1 preferably comprises a base part 1A in which the channel 3 or the microfluidic system is or are formed in particular by one or more depressions—preferably in the form of one or more grooves—which is or are preferably closed off by a cover 1B. In FIG. 2, the liquid 2 is not shown.

The base part 1A is preferably embodied as a plastics part and/or injection moulding. The base part 1A is preferably at least substantially flat, planar, plate-shaped and/or rigid in configuration.

The channel 3 or the microfluidic system is preferably formed in or along a flat side of the base part 1A and/or open towards a flat side. The channel 3 or the depression or flat side is preferably at least substantially totally closed off by the cover 1B. However, other design solutions are also possible.

The cover 1B is preferably embodied as a film. The cover 1B is preferably stuck on, laminated on and/or welded on. Preferably, the cover 1B is formed by an adhesive film or heat-sealable film or the like.

The cover 1B is preferably transparent, at least in parts, for example in order to permit optical detection or examination or the like.

In all the plan views of the device 1, the cover 1B has been omitted for illustration purposes.

The device 1 has at least one body 4 that is movable in the channel 3 or system and/or in the liquid 2.

Figure 3:
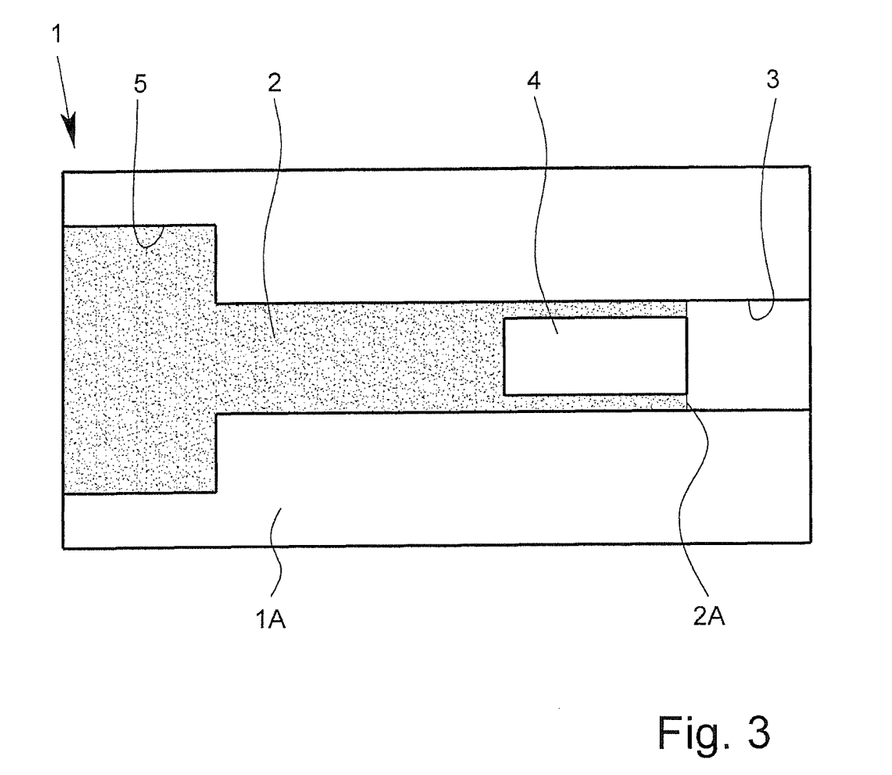
FIG. 3 is a plan view of the device according to the first embodiment in another state.

The body 4 is movable in the channel 3, in particular along the channel 3. The plan view of the device 1 according to FIG. 1 shows the body 4 in a first position. The plan view according to FIG. 3 shows the body 4 in a second or other position.

The proposed device 1 and the proposed method provide that the liquid 2 and, particularly preferably, the front 2A thereof (flowing front) and/or the filling of the channel 3 with the liquid 2 can be manipulated or controlled by means of the movement of the body 4 in the channel 3, particularly depending on the position and/or movement of the body 4. This is particularly made possible or achieved, according to the proposal, by the fact that the liquid 2 does not automatically fill the channel 3, particularly as a result of capillary forces. In particular, the cross section of the channel 3 is chosen to be such (so great) and/or the wettability is chosen to be such (so little) that there is no, or in any case only marginal, flow of the liquid 2, for example starting from a reservoir 5 connected to the channel 3, into the channel 3 by capillary forces, over the relevant period of time. Particularly preferably, the angle of contact of the liquid 2 with the channel wall, formed here by the base part 1A and the cover 1B and optionally also with the body 4 or its surface, is less than 90°.

When the locally variable or movable body 4 is moved into the region of the front 2A in the channel 3, in particular moves out of the liquid 2 beyond the front 2A into the not yet filled channel 3, or is brought into contact for the first time with the liquid 2, starting from the channel 3 which has not yet been filled, the liquid 2 flows into the gap or intermediate space 6 that is present between the channel wall and the body 4. This intermediate space 6 is very narrow or slot-like, in particular. This geometric change to the channel cross section for the liquid 2 in the region of the body 4 leads to an increased pressure gradient within the liquid 2 or to an increased capillary force or to an outflow of the liquid 2 into the intermediate space 6. In particular, such high capillary forces are at work in the intermediate space 6 that the desired outflow of the liquid 2 into the intermediate space 6 takes place in particular relatively or sufficiently rapidly.

If the body 4 in the channel 3 is moved away from the reservoir 5 or from the inflow end of the liquid 2 or from the part of the channel 3 that has already been filled with liquid 2, i.e. to the right, as indicated by the arrow, in the representation in FIG. 1, so that the body 4 remains in contact with the liquid 2 or its front 2A, the liquid 2 streams or flows constantly into the intermediate space 6 that is moving or being formed, and thus into the channel 3. This provides a controlled transporting of the liquid into the channel 3 or permits controlled manipulation of the liquid 2. In particular, the filling of the channel 3 with the liquid 2 or the position and/or movement of the front 2A of the liquid 2 can thus be controlled or manipulated very simply.

FIG. 1 shows the device 1 in a still moving state. The liquid 2 has not yet completely filled the intermediate space 6, but has filled it only partially. The liquid 2 is thus still flowing into the intermediate space 6, in particular, as indicated by the arrow. Alternatively or additionally, this may show that the body 4 itself is still being moved in the direction of the arrow, i.e. into the part of the channel 3 that is not yet filled with liquid 2.

Particularly preferably, the maximum speed of movement of the body 3 is limited so that it is at least not substantially greater than the speed at which the liquid 2 fills the intermediate space 6. In this way it can be ensured that even during a longer movement of the body 4 the contact of the body 4 with the liquid 2 or its front 2A is not broken. However, it is also possible to move the body 4 temporarily faster. However, care must be taken to ensure that this movement does not last too long, so as to avoid the above-mentioned loss of contact with the liquid 2. This can be done for example by correspondingly limiting the maximum travel distance at high speed and/or the maximum time taken for the travel at high speed.

FIG. 3 shows the body 4 in another position. In particular, the intermediate space 6 here is completely full of liquid 2. This is, in particular, a stationary state which is occupied when the body 4 is no longer being moved and the intermediate space 6 has been completely filled with the liquid 2. In this state, the liquid 2 or its front 2A terminates at least substantially with the end of the body 4 that is at the front in the direction of movement, or with the end of the narrow gap or intermediate space 6 for the liquid 2 that is formed between the body 4 and channel wall.

The body 4 has a preferably at least substantially sharp edge or a sharp step at least at its front end in the direction of movement, in order to generate by means of an increase in cross-section that is as abrupt or sharp as possible and thus produce a capillary stop for the liquid 2 or its front 2A, so that the liquid 2 stops in a defined or reliable manner when the intermediate space 6 is completely full. This is to avoid, in particular, the liquid flowing out beyond the body into the channel 3, particularly as a result of capillary forces, and thereby flowing completely around the body 4. Even if this is preferably unwanted, this effect may nevertheless be utilised if necessary, for example if the body 4 is moved up to a corresponding projection, stop or other cross-section of the channel 3 or up to another body 4 in the channel 3 or brought into contact therewith.

The proposed device 1 and the proposed method may also be used to manipulate the liquid 2, particularly by moving the body 4 within the liquid 2 and/or by moving the body 4 out of the liquid 2 and/or moving the body 4 into the liquid 2. Thus, for example, it is possible to mix the liquid 2 or to transfer a specified amount of the liquid 2 or a constituent of the liquid 2.

For moving the body 4, the device 1 preferably comprises a manipulating device 7, as shown in FIG. 2. However, the manipulating device 7 may only be associated with the device 1, in particular it may form part of a separate device.

The movement of the body 4 preferably takes place in contactless manner and more particularly magnetically in the embodiment shown, particularly preferably by the variation of a magnetic field acting on the body 4. In particular, the magnetic field is generated externally. In the embodiment shown, the manipulating device 7 comprises for this purpose at least one external magnet and/or electromagnet or a plurality of electromagnets.

Moreover, the body 4 is preferably produced at least partly from magnetic or magnetisable material, or provided therewith, the material in particular forming a magnet. In particular, a paramagnetic, superparamagnetic or ferromagnetic material is used.

The magnetic material or the magnet may for example be accommodated in the body 4 or glued therein or mounted or glued therein or, for example, cast therein. However, the body 4 may also be made essentially from magnetic or magnetisable material. If necessary, several or different magnetic materials or magnets may also be mounted or used on the body 4, for example spatially distributed or spaced from one another, in particular so as to achieve a certain controllability or mobility of the body 4.

The use of the magnetic material or the magnet may ensure for example that the body 4 is also movable along a gradient of the magnetic field acting on the body 4, i.e. in particular a magnetic field generated by the manipulating device 7, also in particular in an area of high magnetic field strength.

The body 4 can also be moved in a specified direction, into a specified area and/or optionally also in opposite directions, by suitably changing the magnetic field or the gradient of the magnetic field. Correspondingly rapid changes, particularly a change in the direction of the gradient of the magnetic field, can also provide a back and forth motion or reciprocating movement of the body 4 or oscillation of the body 4 which may be very rapid.

Alternatively or additionally, the body 4 can also be moved by any other method, for example by the action of gravity, for example during pivoting or rotation, or by the effect of some other force or acceleration, for example during rotation of the device 1, by electrical attraction or repulsion, by frictional or interlocking engagement on the body 4, for example by means of a filament or other tensioning or compression means, by ultrasound or the like.

The body 4 is preferably movable in the longitudinal direction or along the channel 3 at least or optionally only in one direction or in both directions.

In order to achieve or assist an easy and/or defined movement of the body, particularly in the channel 3 or along the channel 3 or on the bottom of the channel 3 or on the base part 1A, the body 4 optionally comprises at least one guide means 4A which, in the embodiment shown, may be formed by, in particular, a plurality of projections or runners, as indicated in FIG. 2. The guide means 4A or the projections or runners may for example assist with the sliding of the body 4 on the base part 1A or on the bottom of the channel 3, i.e. may reduce the sliding resistance. The guide means 4A may guide or hold the body 4 in particular at a spacing from the bottom of the channel 3, the side walls of the channel 3 and/or the cover 1B.

As required, the guide means 4A may be provided on only one side, particularly on the bottom of the body 4, or on several or all of the sides of the body 4 facing the channel wall. As required, differently configured guide means or projections, runners or the like may also be provided or formed on the various side faces.

To achieve the least possible contact of the body 4 with the channel wall or to achieve the least possible friction, particularly flat and/or calotte-shaped projections are particularly preferred.

Alternatively or additionally, the body 4 may also be guided laterally by the liquid 2 in the channel 3. In particular, it is possible for the liquid 2 to tend to fill the intermediate space 6 between the body 4 and the channel wall, over the entire periphery of the body 4, or towards all the channel walls. This filling may in particular take place automatically, as a result of capillary forces. This filling may for example take place automatically after the body 4 first comes into contact with the liquid 2. As the body 4 then continues to move within the channel 3, the intermediate space 6 then remains at least sufficiently filled with liquid to ensure that the body 4 is preferably guided laterally solely by the liquid 2 and in particular without making contact with the channel wall.

The above-mentioned filling of the intermediate space 6 with the liquid 2 and, in particular, the general lateral filling of the body 4 in the channel 3 with the liquid 2 and/or the rapid filling of the intermediate space 6 with the liquid 2 or rapid advance of the front 2A in the intermediate space 6 may be assisted or achieved by a plurality of measures, in particular by a narrow size or flat configuration of the intermediate space 6 and/or by good or increased wettability of the body 4.

The intermediate space 6 is preferably very thin or narrow or tight in configuration. This produces relatively high capillary forces in the intermediate space 6 which ensure that the liquid 2 fills the intermediate space 6 very quickly and/or preferably on every side around the circumference of the body 4.

To increase or improve the wettability, the body 4 may be correspondingly partially or completely structured, particularly preferably microstructured, treated and/or coated, in particular at least or only on its surfaces and side faces facing the channel wall. In this way it is possible for example to ensure that the side faces of the body 4 are of correspondingly hydrophilic configuration, in the case of a hydrophilic liquid 2, whereas the channel 3 or its channel wall is then of particularly hydrophobic configuration.

To assist or permit the guidance of the body 4 in the channel 3 by means of the liquid 2 and/or to assist or permit the filling of the intermediate space 6 at the bottom, the body 4 preferably has a density that at least substantially corresponds to the liquid 2.

Preferably, the liquid 2 thus forms a film between the body 4 and the channel wall, i.e. in the intermediate space 6, thus enabling the body 4 to be guided laterally.

The body 4 preferably has a cross-section which is at least substantially geometrically similar to the channel cross-section. The optional guide means 4A are preferably not taken into consideration. Thus, a very small intermediate space 6 or one that is uniform over the circumference or cross-section can be achieved or ensured between the body 4 and the channel wall, particularly if the body 4 is at least substantially centrally arranged or guided in the channel 3.

In the embodiment shown, the channel is at least substantially rectangular or square in cross-section. The body 4 is then preferably at least substantially correspondingly configured. However, other cross-sectional shapes may also be used. For example, it is also possible for the channel 3 and the body 4 to have an at least substantially round, oval or flat cross-section.

The body 4 is preferably of elongate configuration. This helps to ensure good guidance in the channel 3.

The body 4 preferably has an at least substantially constant cross-section over its entire length or at least over a large left-hand region thereof.

In the embodiment shown, the body 4 is preferably at least substantially cuboid and/or prism-shaped.

The body 4 preferably comprises at least substantially flat or planar side faces that face the corresponding side walls of the channel wall.

The average or maximum distance of the body 4 or its surface from the channel wall, i.e. the average or maximum height or thickness of the intermediate space 6, is preferably less than 1 mm, more particularly less than 500 µm, particularly preferably approximately 200 µm or less.

The body 4 is preferably guided in a defined alignment in the channel 3 or by means of the channel 3.

Preferably, the body 4 has a length that is greater than the maximum cross-section of the channel 3. Accordingly, the body 4 is guided at least in the lengthwise direction through the channel 3.

Particularly preferably, the body 4 fills the cross-section of the channel 3 by more than 60% in terms of area, more particularly by more than 70% or 80%, as schematically shown in the cross-section according to FIG. 2. This ensures that the intermediate space 6 is very small in cross-section, which is advantageous particularly for filling it with liquid 2.

The body 4 is preferably of dimensionally stable configuration with a defined shape.

The body 3 is preferably made of plastics or is a plastics component. This is favourable in terms of its manufacture or permits the use of a material having the desired properties. For example, the body 4 is made at least substantially of PMA or PE.

The body 3 is preferably an injection moulded part or is produced by injection moulding. This allows cheap and easy manufacture and/or shaping.

If required, the body 4 or at least its surface is made from a luminescent or fluorescent material or is, for example, partially coated therewith. This assists with detection of the body 4.

The body 4 is preferably movable at least substantially in a straight line in the channel 3 and/or movable back and forth in the channel 3. However, it is also possible that the channel 3 does not extend in a straight line but is coiled or meandering or is bent or extends in some other way. The body 4 may then preferably be moved along the channel 3 or in a section or region of the channel 3.

Preferably, only a single movable body 4 is provided in the device 1 or channel 3 or in the system. This contributes to a defined movement. However, it is also possible to provide a plurality of bodies 4 in the channel 3, which are in particular movable independently of one another and allow corresponding manipulation of the liquid 2. For example, the bodies 4 may also be configured differently, for example they may have different cross-sections or sizes and/or be movable in different sections or channels and/or may also be movable together or cooperate with one another, so that for example the intermediate spaces 6 between the bodies 4 and the channel wall can be brought into communication with one another and the liquid 2 can be conveyed or transferred from one intermediate space 6 to another intermediate space 6.

The body 4 may also be movable into different regions or sections of the channel 3 or microfluidic system and/or into different liquids 2.

Particularly preferably, according to the proposal, the body 4 is always moved or manipulated with the front 2A of the liquid 2 or, conversely, the front 2A of the liquid 2 is always moved or manipulated together with the body 4 or by the body 4.

The proposed device 1 and the proposed method can be used for different purposes. Thus, for example, a certain volume of liquid can be placed in the channel 3. Alternatively or additionally, the wetting of the channel 3 can be influenced by the position of the body 4.

Some other embodiments of the proposed device 1 and methods and uses will be described in more detail hereinafter by means of the additional Figures. The previous remarks and explanations apply accordingly and in a supplementary manner, even though the corresponding description has not been included, to avoid repetition.

Figure 4:
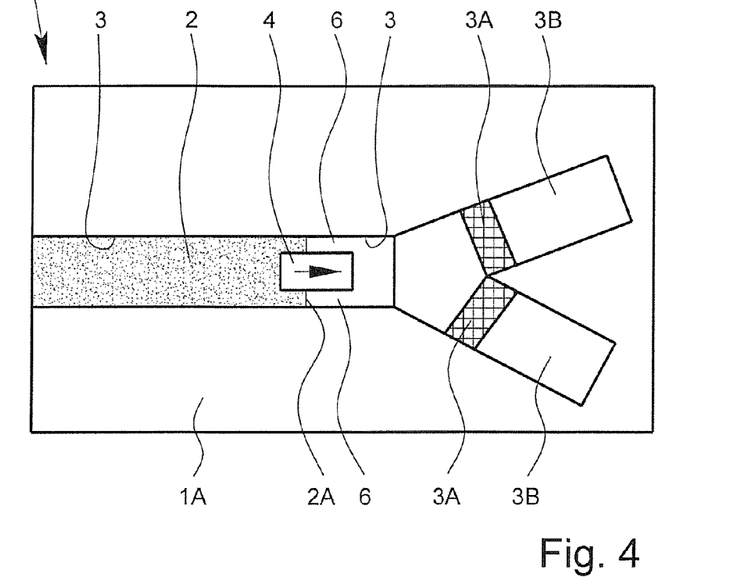
FIG. 4 is a plan view of the proposed device according to a second embodiment.
Figure 5:
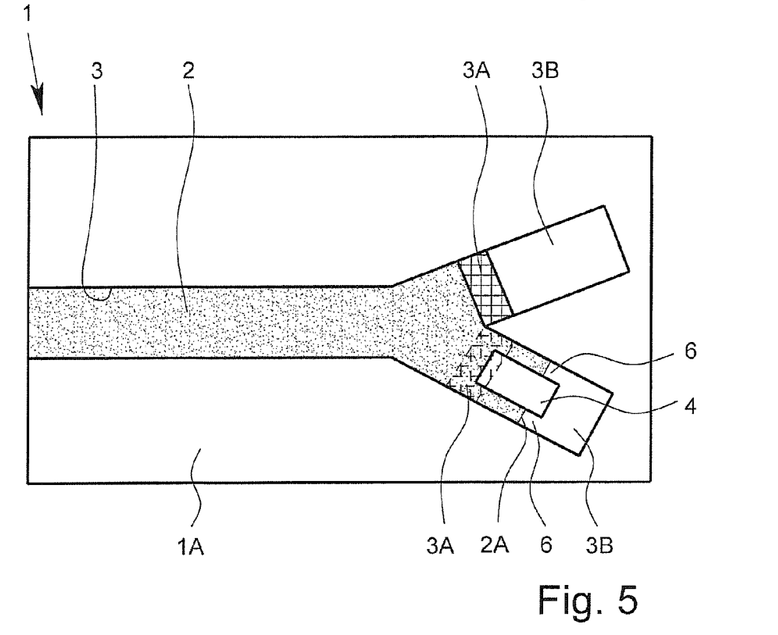
FIG. 5 is a plan view of the device according to the second embodiment in another state.

FIGS. 4 and 5 each show a plan view of the proposed device 1 according to a second embodiment, the body 4 being shown in various positions.

The channel 3 in the second embodiment comprises at least one non-wettable region 3A which can be bridged for the liquid 2 by means of the body 4.

In the embodiment shown the channel 3 has two or more branches or channel sections 3B and/or two or more non-wettable regions 3A. Preferably, the body 4 is selectively movable into one of the two channel sections 3B and/or over at least one of the two regions 3A. In the embodiment shown the channel sections 3B are connected to a main section of the channel 3 for example by means of a branch connecting them to one another, the body 4 being selectively movable into one of the channel sections 3B, as shown in FIG. 5.

The body 4 may for example be moved temporarily or permanently over or onto a non-wettable region 3A, as shown in FIG. 5. In this way the corresponding region 3A is preferably bridged, so that the liquid 2 can flow, in particular, over the body 4 or through the intermediate space 6 over the non-wettable region 3A into the adjoining channel or channel section 3B, as shown in FIG. 5.

In order to bridge the non-wettable region 3A by means of the body 4, the body 4 is preferably moved over or onto the non-wettable region 3A, so that the liquid 2 can flow through the intermediate space 6 over the region 3A into the adjoining channel 3 or channel section 3B.

Preferably, the body 4 has a longer length in the longitudinal direction of the channel than the non-wetting region 3A, so that the body 4 is preferably able to cover the region 3A completely and in particular can project on both sides into the adjoining channel region, in order to bridge the region 3A fluidically—i.e. for the liquid 2—in such a way that the liquid 2 is able to flow away over the region 3A.

The non-wettable region 3A may if necessary be formed only on the bottom of the channel 3 or optionally over the entire cross-section or circumference of the channel 3, i.e. also on the side walls and on the lid 1B, for example, in addition to the bottom.

The non-wettable region 3A is particularly preferably formed by a corresponding coating and/or treatment of the respective material.

By the term "non-wettable" is meant, in particular, according to the proposal, that the wetting of the region 3A by the liquid 2 is so poor or the contact angle is so small that the liquid 2 does not flow away over this region 3A into the adjoining channel 3 or channel section 3B. Rather, it requires bridging by the body 4.

Depending on the configuration, it may be such that after a first wetting or bridging of the region 3A, a permanent fluid connection or flow over the region 3A is made possible, even if the body 4 no longer bridges the region 3A. However, it is also possible for this fluid connection or flow over the region 3A to be maintained only when, or as long as, the body 4 also bridges this region.

When the body 4 is moved away again, for example moved on, as shown in FIG. 5, or moved back again, for example into the section of the channel 3 that has already been filled with liquid 2, the fluid connection over the region 3A may also be interrupted directly again or may be broken automatically. This depends particularly on the capillary forces or on the wettability and dimensions, for example of the region 3A.

If necessary, in the second embodiment the body 4 may also be moved back into the main section of the channel 3 and then into the other channel section 3B, in this case into the upper channel section 3B, so as to bridge the other non-wettable region 3A (too) for the liquid 2.

It is also possible that a plurality of non-wettable regions 3A are arranged or formed one behind the other, at a spacing from one another, in the channel, and can be bridged for the liquid 2 by means of the body 4, particularly one after the other. Thus, for example, a correspondingly controlled or manipulated forward flow of the liquid 2 in the channel 3 can be achieved, in order, for example, to carry out and/or run various reactions, detections or the like one after the other in channel sections 3A located behind one another.

In the second embodiment, the body 4 is preferably selectively or successively movable into at least one or into several regions or sections 3B of the channel 3.

In the third embodiment, explained hereinafter with reference to FIGS. 6 to 8, the device 1 comprises at least one, preferably several side channels 3C, which branch off, in particular, laterally from the channel 3 and/or preferably have a smaller cross-section in relation to the channel 3. By corresponding positioning or movement of the body 4 along the channel 3 it is possible to supply, or fluidically connect, a desired side channel 3C or the side channels 3C with the liquid 2.

Figure 6:
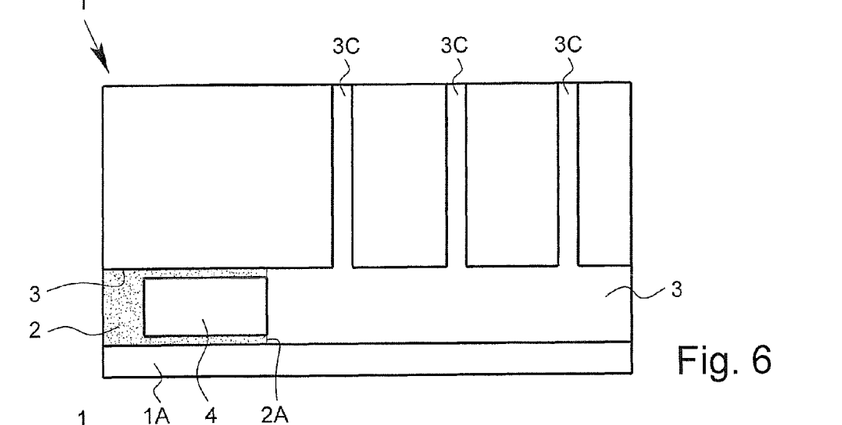
FIG. 6 is a plan view of the proposed device according to a third embodiment.

In the plan view according to FIG. 6, the body 4 with the front 2A is still at a distance from the first side channel 3C, so that the liquid cannot flow into this side channel 3C.

Figure 7:
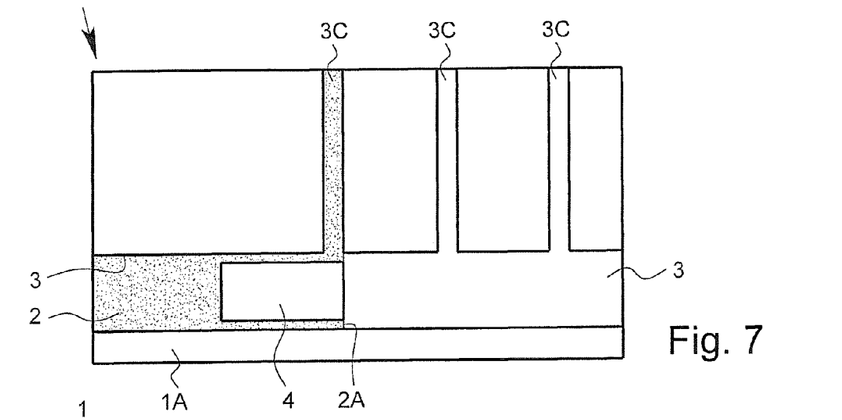
FIG. 7 is a plan view of the device according to the third embodiment in another state.

In the plan view according to FIG. 7, the body has been moved further forwards and has reached the first side channel 3C, so that it is now fluidically connected or the liquid 2 is able to flow, or has flowed, into the side channel 3C, as shown in FIG. 7.

Figure 8:
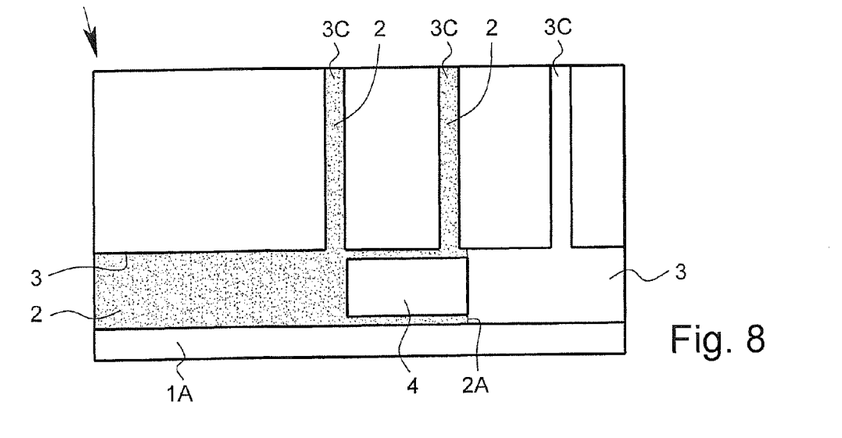
FIG. 8 is a plan view of the device according to the third embodiment in yet another state.

In the plan view according to FIG. 8, the body 4 is in a further advanced position, adjacent to the next side channel 3C, so that this is now also connected to the liquid 2 or is being filled with the liquid 2 or has already been filled, as shown in FIG. 8.

The influx of liquid 2 into a side channel 3C of the channel 3 is thus controlled by the body 4, while the liquid 2 only flows into the side channel 3C when the body 4 is being moved or has been moved with the liquid 2 in the channel 3 at least up to the point where the side channel 2C branches off from the channel 3.

Thus, by means of the proposed device 1 and the proposed method, it is possible selectively to supply individual channel portions 3B or side channels 3C or the like with the liquid 2. This can be done in particular by selective attachment or connection and/or bridging of a non-wettable region 3A, or the like.

Alternatively or additionally, the proposed device 1 and the proposed method may also be used to meter the liquid 2, particularly by corresponding movement of the body 4 and/or by selective filling of corresponding metering regions or chambers.

Individual features of the different embodiments and the embodiments themselves may be combined with one another as desired, but may also be implemented or used independently of one another.

LIST OF REFERENCE NUMERALS

1 device
1A base part
1B cover
2 liquid
2A front
3 channel
3A non-wettable region
3B channel section
3C side channel
4 body
4A guide means
5 reservoir
6 intermediate space
7 manipulating device

The invention claimed is:

1. A device (1) for the manipulation of a liquid (2), having a channel (3) for receiving the liquid (2) and having a body (4) that is movable in the channel (3), characterised in that the body (4) fills the channel (3) by more than 60% of its cross-sectional area and an intermediate space (6) is formed between the body (4) and the channel wall, so that the liquid (2) or its front (2A) is held in the intermediate space (6) by capillary forces and the channel (3) is filled with the liquid (2) only up to the body (4) or end of the intermediate space (6), and/or in that the channel (3) comprises at least one non-wettable region (3A) which is bridged for the liquid (2) by means of the body (4).

2. The device according to claim 1, characterised in that the body (4) is guided in a defined alignment in the channel (3).

3. The device according to claim 1, characterised in that the body (4) is laterally guided by a film of the liquid (2) between the body (4) and the channel wall.

4. The device according to claim 1, characterised in that the body (4) has a length that is greater than the maximum width of the channel (3).

5. The device according to claim 1, characterised in that the body (4) is of elongate configuration.

6. The device according to claim 1, characterised in that the body (4) is movable magnetically and/or in a contactless manner.

7. The device according to claim 1, characterised in that a manipulating device (7) is provided for moving the body (4) along the channel (3).

8. The device according to claim 1, characterised in that the body (4) is selectively movable into different regions or sections (3B) of the channel (3).

9. The device according to claim 1, characterised in that a side channel (3C) branches off from the channel (3), while the liquid (2) only flows, or is able to flow, into the side channel (3C) when the body (4) is, or has been, moved with the liquid (2) in the channel (3) at least up to the branching of the side channel (3C) from the channel (3).

\* \* \* \* \*